| United States Patent [19] | [11] Patent Number: 4,541,961 |
|---|---|
| Davidson | [45] Date of Patent: Sep. 17, 1985 |

[54] NITRILE PURIFICATION

[75] Inventor: Robert I. Davidson, Baton Rouge, La.

[73] Assignee: Ethyl Corporation, Richmond, Va.

[21] Appl. No.: 526,964

[22] Filed: Aug. 29, 1983

[51] Int. Cl.$^4$ .............................................. C07C 121/66
[52] U.S. Cl. ............................ 260/465 G; 260/465 R; 260/465 D; 260/465 E; 260/465 F; 260/465 H
[58] Field of Search ........... 260/465 R, 465 F, 465 G, 260/465.1, 465 D, 465 E, 465 H

[56] References Cited

U.S. PATENT DOCUMENTS 4,370,278  1/1983  Stahly et al. .................... 260/465 E

*Primary Examiner*—Dolph H. Torrence
*Attorney, Agent, or Firm*—Donald L. Johnson; John F. Sieberth; Patricia J. Hogan

[57] ABSTRACT

Nitriles, such as 2-(2-fluoro-4-biphenyl)propionitrile, contaminated with ketones having similar boiling points are purified by treating the nitrile/ketone mixture with an alkali metal borohydride, e.g., sodium borohydride, to complex the ketone. After complexing of the ketone, the nitrile can be separated therefrom by distillation.

9 Claims, No Drawings

NITRILE PURIFICATION

TECHNICAL FIELD

This invention relates to nitriles, especially 2-phenylalkyl cyanides, and more particularly relates to a method of purifying them.

BACKGROUND

Nitriles can be prepared by various techniques that result in the co-formation, or subsequent formation, of ketone impurities having boiling points so similar to the boiling points of the nitriles that simple distillation is not an effective way of purifying them. Among the nitrile syntheses that result in such impure nitriles are:

(A) the nucleophilic substitution reactions of U.S. Pat. No. 4,370,278 (Stahly et al. I); copending applications Ser. No. 452,518 (Stahly et al. II), Ser. No. 452,615 (Stahly), and Ser. No. 452,618 (Stahly et al. III), all filed Dec. 23, 1982; Ser. No. 474,138 (Stahly et al. IV), filed Mar. 10, 1983; and Ser. Nos. 487,039 (Lilje I) and 487,038 (Lilje II), both filed Apr. 21, 1983, and (B) the Gomberg and pseudo-Gomberg processes disclosed in Stahly et al. I and copending applications Ser. Nos. 488,192 (Ramachandran I) and 488,068 (Ramachandran II), both filed Apr. 25, 1983, and Ser. No. 523,161 (Davidson) and Ser. No. 523,450 (Herndon), both filed Aug. 15, 1983.

SUMMARY OF THE INVENTION

An object of this invention is to provide a novel process for purifying nitriles contaminated with ketones having similar boiling points.

Another object is to provide such a process which is simple and economical.

These and other objects are attained by treating a mixture of a nitrile and a ketone having similar boiling points with an alkali metal borohydride.

DETAILED DESCRIPTION

The nitrile/ketone mixture treated in accordance with the present invention can be any nitrile/ketone mixture wherein the nitrile and ketone have boiling points so similar as to make simple distillation an ineffective way of separating them. However, in a preferred embodiment of the invention, it is a ketone-contaminated 2-phenylalkyl cyanide such as is prepared by processes like the nucleophilic substitution processes of Stahly, Stahly et al. I, II, III, and IV, and Lilje I and II and the Gomberg and pseudo-Gomberg processes of Stahly et al. I, Ramachandran I and II, Davidson, and Herndon, the teachings of all of which are incorporated herein by reference.

In general, the preferred 2-phenylalkyl cyanides are compounds corresponding to the formula:

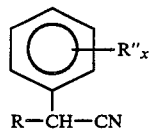

wherein R is hydrocarbyl, i.e., alkyl, cycloalkyl, aryl, aralkyl, alkaryl, etc. (generally an alkyl group containing 1–6 carbons); R" substituents are independently selected from hydrogen and innocuous substituents, i.e., substituents that are inert to alkali metal borohydrides, such as hydroxy, halo (i.e., chloro, bromo, fluoro, or iodo), nitro, amino, cyano, carboxy, hydrocarbyl (especially phenyl, substituted phenyl, or an alkyl of 1–6 carbons), hydrocarbyloxy, etc.; and x is an integer of 1–5—any combination of hydrogens and innocuous substituents being encompassed by the R" designation.

In a particularly preferred embodiment of the invention, the 2-phenylalkyl cyanides are 2-biphenylalkyl cyanides corresponding to the formula:

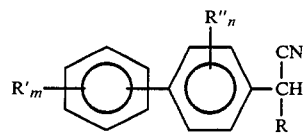

wherein R is hydrocarbyl, i.e., alkyl, cycloalkyl, aryl, aralkyl, alkaryl, etc. (generally an alkyl group containing 1–6 carbons); R' and R" are independently selected from hydrogen and innocuous substituents, i.e., substituents that are inert to alkali metal borohydrides, such as hydroxy, halo (i.e., chloro, bromo, fluoro, or iodo), nitro, amino, cyano, carboxy, hydrocarbyl (especially an alkyl of 1–6 carbons), hydrocarbyloxy, etc.; m is an integer of 1–5; and n is an integer of 1–4—any combination of hydrogens and innocuous substituents being encompassed by the designation R' and R".

Particularly preferred among such compounds are substituted and unsubstituted 2-(4-nitro- and 4-aminobenzene)propionitriles, including those bearing fluoro, chloro, phenoxy, or any of the other substituents indicated above, such as the compounds specifically or inherently disclosed in Stahly, Stahly et al. I, II, III, and IV, and Lilje I and II; 2-(4-biphenyl)alkyl cyanides, especially halo-substituted 2-(4-biphenyl)propionitriles, such as 2-(2-fluoro-4-biphenyl)propionitrile and other such compounds specifically or inherently disclosed in Stahly et al. I, Ramachandran I and II, Davidson, and Herndon; etc.

The ketones apt to be found in admixture with the nitriles are ketones which have boiling points and structures quite similar to those of the nitriles. Thus, in the case of the preferred biphenylalkyl cyanides, the ketone contaminants are generally acylbiphenyls corresponding to the formula:

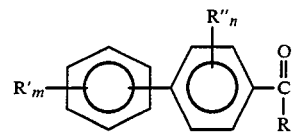

wherein R, R', R", m, and n have the same meanings as given above.

The alkali metal borohydride used in the practice of the invention may be any alkali metal borohydride but is generally sodium borohydride. This ingredient is employed in at least the stoichiometric amount required to complex the ketone impurity, i.e., one mol per four mols of ketone, and is usually employed in a 10–50% excess of that amount, e.g., about a 30% excess.

The treatment of the nitrile/ketone mixture with the alkali metal borohydride is suitably accomplished at ambient temperatures in an appropriate solvent, e.g., an alkanol such as ethanol. This treatment results in complexing the ketone to make it non-volatile so that it can be separated from the nitrile by subjecting the nitrile to distillation. Then, when separation of the nitrile and complexed ketone is desired, the separation is readily accomplished by removing the solvent, e.g., by evaporation, and distilling the nitrile from the mixture.

The following example is given to illustrate the invention and is not intended as a limitation thereof.

EXAMPLE

A 52.7 g portion of a mixture consisting of 75% of 2-(2-fluoro-4-biphenyl)propionitrile, 22% of 4-acetyl-2-fluorobiphenyl, and 3% of other impurities was dissolved in 200 ml of ethanol by heating to 60° C. The yellow solution was allowed to cool to ambient temperature and was then treated with a 2.7 g portion of sodium borohydride. Instantaneous bubbling and a red color resulted. Analysis of the solution indicated that no ketone remained. The mixture was concentrated to dryness on a rotary evaporator and distilled through a short-path distillation apparatus at 2–3 mm. Only trace amounts of ketone were observed in any of the fractions.

It is obvious that many variations may be made in the products and processes set forth above without departing from the spirit and scope of this invention.

I claim:

1. A process for separating a nitrile from a ketone having a boiling point so similar as to make simple distillation an ineffective way of separating them, which process comprises treating the nitrile/ketone mixture with an alkali metal borohydride so as to complex the ketone.

2. The process of claim 1 wherein the nitrile is a 2-phenylalkyl cyanide.

3. The process of claim 2 wherein the nitrile is a 2-biphenylalkyl cyanide and the ketone is an acylbiphenyl.

4. The process of claim 3 wherein the nitrile is a 2-(4-biphenyl)propionitrile and the ketone is a 4-acetylbiphenyl.

5. The process of claim 4 wherein the nitrile is 2-(2-fluoro-4-biphenyl)propionitrile and the ketone is 4-acetyl-2-fluorobiphenyl.

6. The process of claim 1 wherein the alkali metal borohydride is sodium borohydride.

7. The process of claim 1 wherein the nitrile is 2-(2-fluoro-4-biphenyl)propionitrile, the ketone is 4-acetyl-2-fluorobiphenyl, and the alkali metal borohydride is sodium borohydride.

8. The process of claim 1 wherein a solution of the nitrile/ketone mixture is treated with an alkali metal borohydride to complex the ketone, the solvent is removed, and the nitrile is separated from the complexed ketone by distillation.

9. The process of claim 7 wherein an ethanolic solution of a 2-(2-fluoro-4-biphenyl)propionitrile/4-acetyl-2-fluorobiphenyl mixture is treated with sodium borohydride to complex the ketone, the solvent is removed, and the nitrile is separated from the complexed ketone by distillation.

* * * * *